United States Patent [19]
Edmundson

[11] Patent Number: 5,391,139
[45] Date of Patent: Feb. 21, 1995

[54] REAL TIME RADIATION TREATMENT PLANNING SYSTEM

[75] Inventor: Gregory K. Edmundson, Farmington Hills, Mich.

[73] Assignee: William Beaumont Hospital, Royal Oak, Mich.

[21] Appl. No.: 201,484

[22] Filed: Feb. 23, 1994

Related U.S. Application Data

[63] Continuation of Ser. No. 940,077, Sep. 3, 1992, abandoned.

[51] Int. Cl.$^6$ ............................................... A61B 6/00
[52] U.S. Cl. .......................................... 600/7; 600/3; 364/413.26
[58] Field of Search .............................. 600/3, 7, 1–2, 600/4–6, 8, 10; 128/898, 653.1; 607/154; 364/413.26

[56] References Cited

U.S. PATENT DOCUMENTS

| | | |
|---|---|---|
| 3,847,138 | 11/1974 | Gollub . |
| 4,244,357 | 1/1981 | Morrison . |
| 4,245,646 | 1/1981 | Ionnou et al. . |
| 4,280,494 | 7/1981 | Cosgrove, Jr. et al. . |
| 4,292,960 | 10/1981 | Paglione . |
| 4,397,314 | 8/1983 | Vaguine ........................... 128/804 X |
| 4,562,829 | 1/1986 | Bergner . |
| 4,624,846 | 11/1986 | Goldenberg . |
| 4,798,209 | 1/1989 | Klingenbeck et al. . |
| 4,815,448 | 3/1989 | Mills . |
| 4,976,680 | 12/1990 | Hayman et al. ........................ 600/7 |
| 5,080,101 | 1/1992 | Dory . |
| 5,084,001 | 1/1992 | Hooft et al. . |
| 5,107,839 | 4/1992 | Houdek et al. . |
| 5,205,289 | 4/1993 | Hardy et al. ........................ 600/7 X |

FOREIGN PATENT DOCUMENTS

1392696A1 5/1990 U.S.S.R. .

*Primary Examiner*—Angela D. Sykes
*Attorney, Agent, or Firm*—Harness, Dickey & Pierce

[57] ABSTRACT

A radiation treatment planning system utilizes a standard interface circuit to continuously digitize and display image data generated by an anatomical imaging device, such as an ultrasound unit. The acquired image data includes positional information of one or more radiation delivery devices relative to an anatomical area to be treated. The acquired data is processed to rapidly determine a radiation dose plan, which is displayed in real time as a superimposed image over the image of the anatomical area being treated.

22 Claims, 5 Drawing Sheets

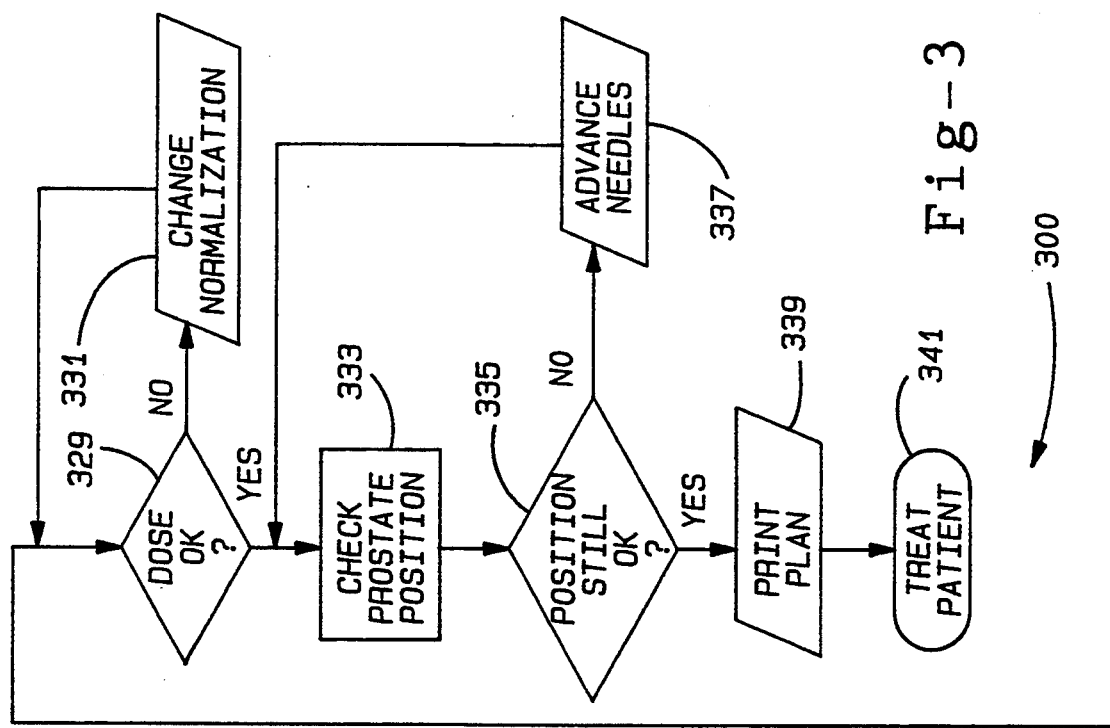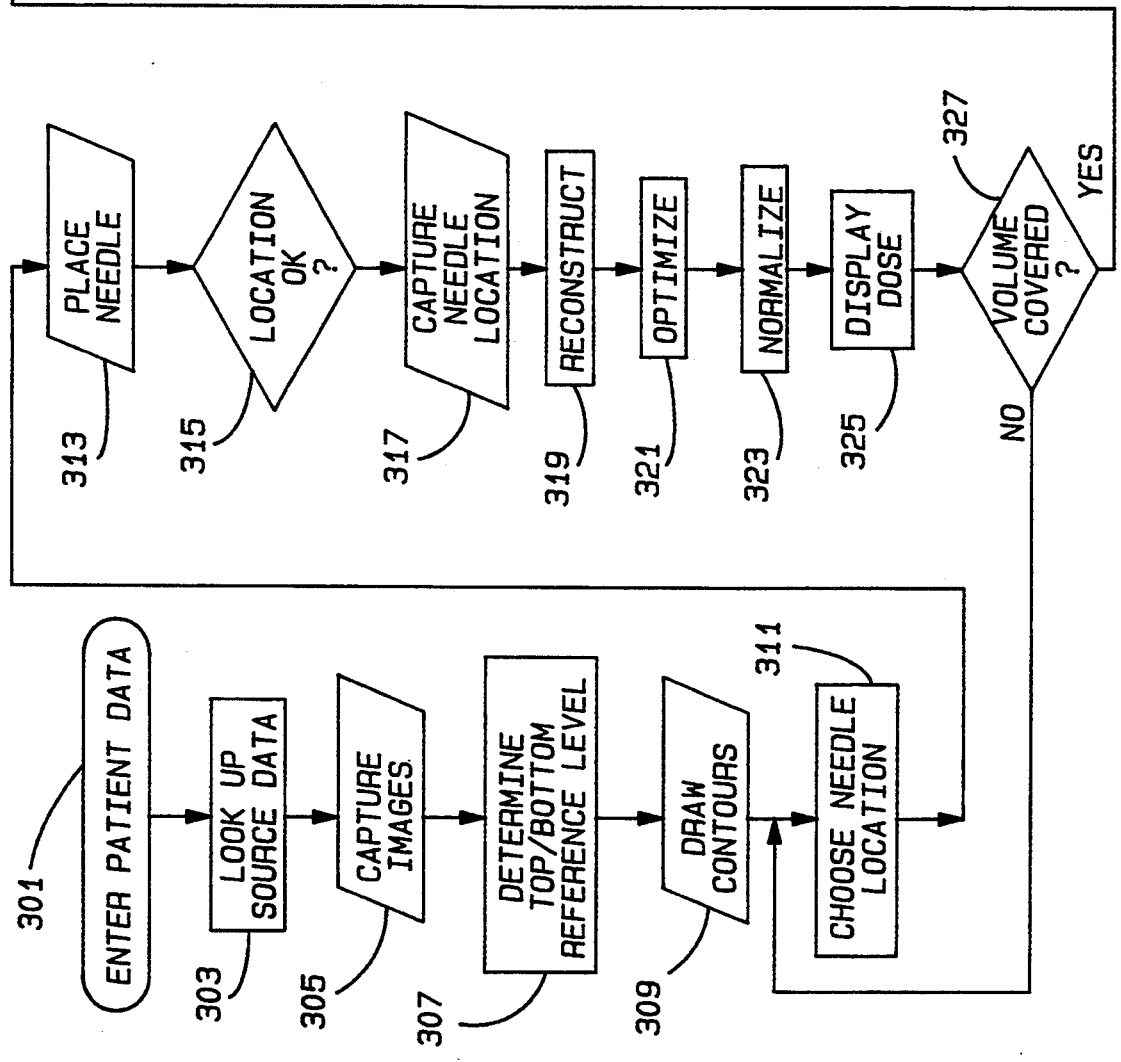

REAL TIME RADIATION TREATMENT PLANNING SYSTEM

This a continuation of U.S. patent application Ser. No. 07/940,077, filed Sep. 3, 1992, now abandoned.

BACKGROUND OF THE INVENTION

The present invention relates to an apparatus and method for effecting radiation dosage planning to be used in rendering radiation treatment to a selected anatomical portion of an animal body, for example, the human prostate gland.

The prior art teaches treatment of localized malignancies with radiation emitted from a discrete radioactive source placed near the malignancy, such treatment commonly referred to as brachytherapy. Since the radioactive sources used in such treatment may constitute a hazard to the personnel administering same, apparatus is now commercially available which allows for the positioning of the radioactive source and the treatment therewith in the patient with minimum radiation exposure to the medical personnel rendering the treatment. Such apparatus allows the positioning and treatment with a radioactive source in the patient after the person administering the treatment moves away from the operating room in which the patient is being treated. Because the radioactive source is loaded into the patient after the medical personnel leave the area, such treatment delivery devices are generally referred to as after-loading devices.

The most recent commercially available radiation delivery devices in the after-loading category utilize a single high dose rate (HDR) source positioned at a plurality of preselected dwell positions within the anatomical part being treated for preselected dwell times. One such radiation delivery HDR after-loading device is commercially available from Nucletron Corporation of Columbia, Md. and is described in U.S. Pat. No. 5,084,001.

The positioning of the HDR source requires a radiation treatment plan which specifies the locations of the HDR source and the time period or dwell time at each such location at which the HDR source is to reside during treatment of the patient. Conventionally, medical personnel place a number of guide tubes or hollow needles for carrying the HDR source into the anatomical area to be treated, take X-rays of the needles in place and then manually digitize the X-ray data utilizing a mouse or courser for input to a dosage planning computer associated with the radiation delivery unit. A disadvantage of this conventional approach is the time required for such data digitization and entry. Data entry time has been found to be on the order of one hour. This delayed time period forces the delivery system to be in place with the patient for a prolonged time prior to actual administration of the treatment radiation dosages. Additionally, in the prior art, there is no provision for on-the-spot adjustments to the delivery system and/or its dosage plan using an interactive visual data system.

There is therefore seen to be a need for an apparatus and method for rapidly, reliably and interactively generating a radiation dosage plan based on real time data associated with a preselected placement of a radiation source delivery system with respect to the anatomical portion to be treated.

SUMMARY OF THE INVENTION

Accordingly, in one aspect of the invention, a real time radiation treatment dosage planning system for use in effecting radiation therapy of a preselected anatomical portion of an animal body includes a radiation delivery device for placing a radiation source at a plurality of positions within a volume of the anatomical portion, an imaging device for generating visual image data corresponding to the anatomical portion, and a processing unit, including a visual image data capturing element, operative to automatically generate in real time, in accordance with captured visual image data, a treatment plan including strength of the radiation source and time periods for which the radiation source is to be placed at each position by the radiation delivery unit.

In accordance with another aspect of the invention, a method for generating a radiation treatment dosage plan for use in applying radiation to a preselected anatomical portion of an animal body by a radiation delivery system operable to place a radiation source in a plurality of positions within a volume of the anatomical portion includes the steps of generating visual image data corresponding to the anatomical portion with a scanner, capturing the visual image data at a stored program processor and automatically generating, using the captured visual data, time periods during which the radiation source is to be placed at each of the positions, and transmitting an indication of the values of the radiation time periods to the radiation delivery system.

It is a feature of the invention that it enables localization techniques suitable for use in the operating room, very rapid reconstruction approaches to generating spatial coordinate data for the positions of the radiation source, rapid and reliable dose optimization, a fast and reproducible method of specifying a prescription dosage, and rapid calculation and display of the resulting dose distribution as an overlay to an image of the anatomical portion being treated. The calculation time for the dose distribution plan is greatly reduced by using scanner data itself for direct loading into a dosage calculation computer.

BRIEF DESCRIPTION OF THE DRAWINGS

The objects and features of the invention will become apparent from a reading of a detailed description taken in conjunction with the drawings, in which:

FIG. 3 is an overall flow chart of a method for real time dosage planning according to the principles of the invention and for use with radiation treatment of a human prostate gland;

DETAILED DESCRIPTION

Figure 1:
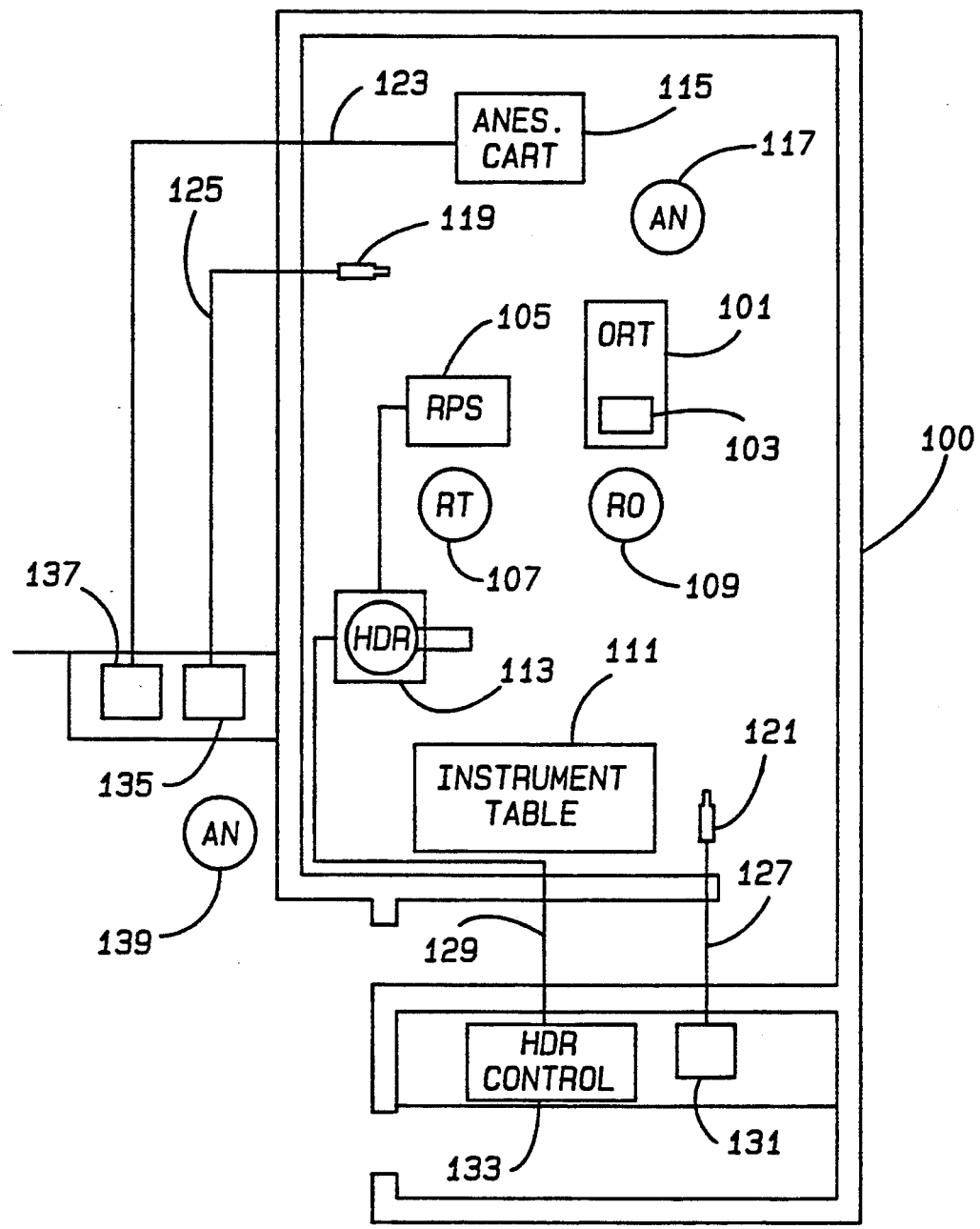
FIG. 1 is a block diagram of an operating room and remote monitoring facility containing apparatus arranged in accordance with the principles of the invention.

With reference to FIG. 1, an overall floor plan layout 100 of an operating room with remote monitoring facilities for use in radiation oncology is depicted. The patient is placed on an operating table 101 having an overhead TV monitor 103 for use by a radiation oncologist 109. The oncologist and a radiation technician or other medical personnel at 107 utilize a real time planning system unit 105 in conjunction with HDR radiation delivery unit 113 for effecting subsequent radiation treatment after the medical personnel have left the operating room.

An anesthetist is positioned at location 117 and utilizes conventional anesthesia equipment located at anesthesia cart 115. Monitoring of the anesthesia equipment from a remote location is effected via data link 123 which runs to a remote anesthesia monitoring station at 139 which includes a remote control 137 and a TV monitor 135 which is coupled to a TV camera 119 in the operating room via bus 125. A remote treatment control center has an HDR delivery control unit 133 and a TV monitor 131 which are coupled to HDR unit 113 and a second TV camera 121 via buses 129 and 127, respectively.

Optionally, the real time dosage planning hardware 105 may be directly coupled to a control unit of HDR delivery unit 113 for direct down loading of dose planning data.

HDR delivery unit 113 comprises, for example, apparatus as disclosed in the abovereferenced U.S. Pat. No. 5,084,001, which is hereby incorporated by reference. As set forth in U.S. Pat. No. 5,084,001, HDR source 113 includes a moving or indexing apparatus such as a stepper motor for moving a radiation source assembly along a plurality of guide tubes extending therefrom and having remote ends which are implantable in a preselected anatomical portion of a patient, typically using access through at least one orifice in the patient's body and positioned such that the end portion is near the site of intended therapy. A control unit of apparatus 113 is capable of causing the source assembly to (a) be moved from a standby position to the end portion of each guide tube and positioned at each of a series of preselected discrete steps lying within the end portion of each guide tube, (b) allowing the source assembly to remain at each of the preselected positions for a preselected residence or dwell time, and (c) causing the source assembly to be withdrawn from the end portion of each guide tube to a rest position.

Figure 2:
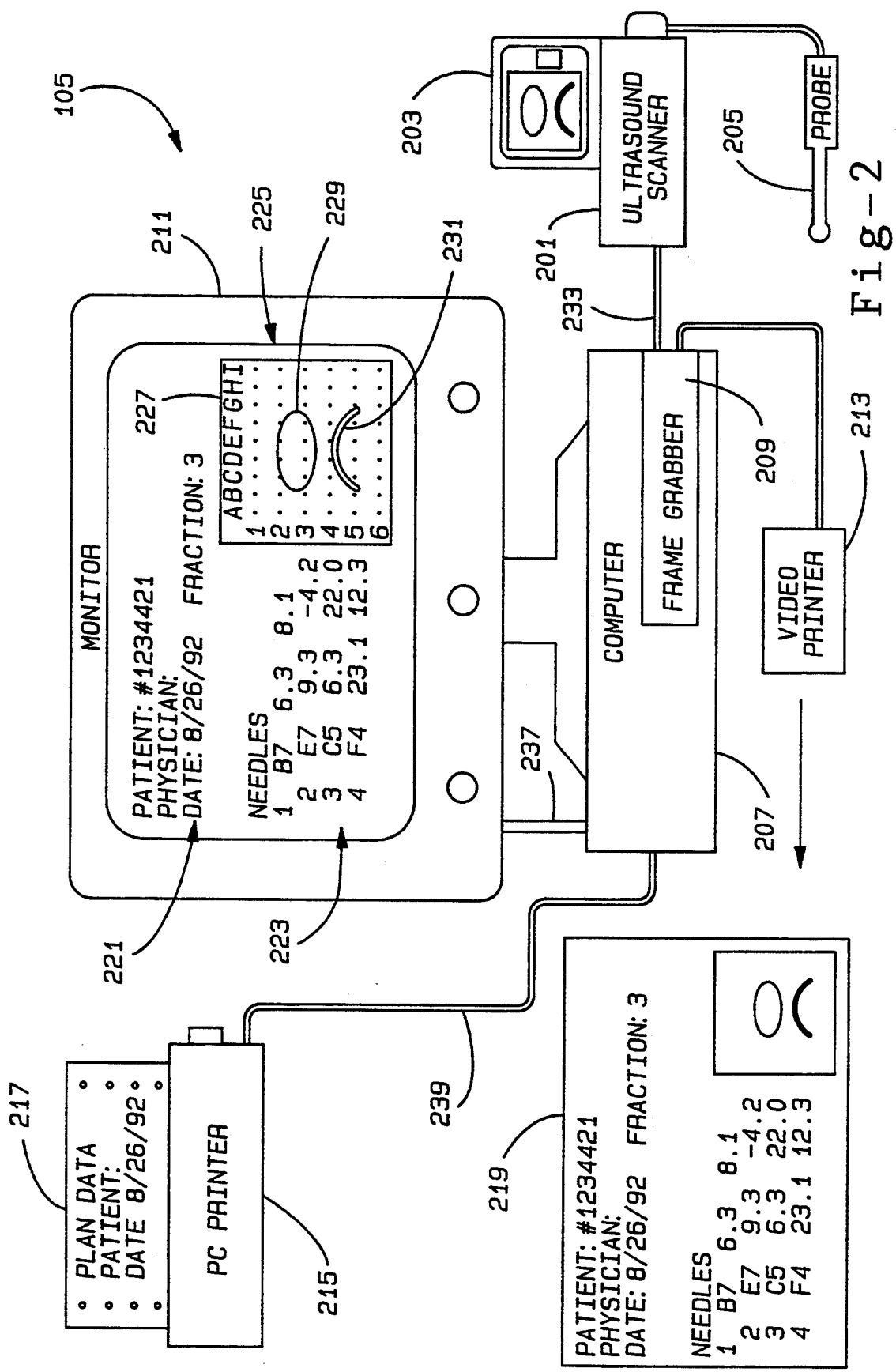
FIG. 2 is a more detailed block diagram of real time radiation dosage planning system hardware arranged in accordance with the principles of the invention.

Further details of the apparatus of real time planning system 105 of FIG. 1 are set forth in the block diagram of FIG. 2. In this specific exemplary embodiment, the prostate gland of a human patient is to be treated. With reference to FIG. 2, video data for use by the apparatus and method of the invention is generated by means of an ultrasound scanner 201 and associated ultrasound probe 205, the scanner including a video display unit 203 which displays the prostate gland 229, a section of the rectal cavity 231, both being overlaid by a grid 227 whose use will be discussed at a later section of this description.

Video data generated by scanner 201 is coupled via bus 233 to a "frame grabber" or video adapter board 209 of computer 207. Computer 207 is additionally coupled via bus 237 to a monitor 211 which displays patient and radiation delivery guide tube information, along with a reconstructed image of the anatomy to be treated at window 225. The patient and physician data is in section 221 of the display, while the coordinate positioning of the radiation delivery needles or guide tubes is set forth at portion 223 of the display. Additionally, a dosage profile resulting from the automatically generated dosage plan is displayed at window 225 in overlay fashion with respect to the image of the anatomical part being treated.

Computer 207 may additionally be coupled via a bus 239 to a standard printer 215 for generating hard copy 217 of the generated dosage plan. Computer 207 may also be coupled via bus 235 to a video printer 213 operable to produce a hard copy of the visual data presented at monitor 211. An example of such hard copy is shown at 219.

Ultrasound scanner 201 could, for example, comprise a Kretz Combison 310a scanner and transrectal transducer probe and bifocal multiplane rectal transducer IRW177 AK/A, available from Kretz Technik AG of Austria. A suitable computer has been found to be the Dell 486P/66 i 486 DX2, a 66 MHz system available from Dell Computer Corporation of Austin, Tex. The frame grabber 209 is a desk top video adapter and could comprise, for example, a commercially available unit available from Cardinal Technologies, Inc. of Lancaster, Pa.

An exemplary embodiment of a general overall dosage planning procedure is set forth in the flow chart of FIG. 3. With reference to FIG. 3 (and the apparatus depicted in FIGS. 1 and 2) the procedure is initiated at step 301 by entry of patient data into computer 207. At step 303 the radiation source data is referenced. This data has been previously entered at computer 207.

Image data from ultrasound scanner 201 of FIG. 2 is then continuously captured at step 305 by frame grabber unit 209 of computer 207 (FIG. 2). At this point, the medical personnel in operating room 100 determine, using the displayed video data, a top and bottom reference level for the anatomical portion, such as the prostate gland, to be treated, and then draw contours of the anatomical portion at step 309 on the reference image displayed at monitor 211 using conventional data entry apparatus such as a mouse unit.

Next, at step 311, the medical personnel choose a candidate radiation source guide tube or needle location using predetermined placement rules which have been empirically determined from experience. The guide tube or needle is then inserted via a template pad by HDR unit 113. Alternatively the dosage planning system can proceed with its calculations and interactive display of a dosage profile without actual implantation of the needles, thereby enabling the medical personnel to judge the acceptability of theoretical results prior to such implantation. At step 315 the medical personnel visually confirm that the needle location is acceptable by viewing a visual representation of a transverse section of the needle and surrounding anatomical tissue generated by the ultrasound scanner unit.

At step 317 the position of the needle is captured at computer 207 utilizing a courser or mouse in conjunction with the video display at monitor 211. Next, at steps 319 through 325, a tentative real time dosage plan comprising a specification of dwell time periods at each dwell position of the radiation source within all presently implanted guide tubes or needles is generated by computer 207.

This automatic generation includes step 319 for reconstructing a model of the three dimensional structure of the dwell positions in the needles implanted so far, an optimization step 321 for determining relative dwell times of the source at each dwell position, and a normalization step 323 in which relative dwell times may be converted to actual dwell times. The dosage profile resulting from the plan thus far is then displayed at monitor 211 at step 325 of FIG. 3. If the final plan has been determined, then a hard copy of this display may be generated by video printer 213.

At decision block 327 the displayed dosage profile which is superimposed at window 225 of monitor 211 over the anatomical portion, such as the prostate gland, to be treated, is viewed by the medical personnel, and if an acceptable dose profile covers an acceptable portion of the anatomical volume, then the procedure advances to step 329. Otherwise, a new needle location is chosen at step 311 and the steps 313 through 325 are re-executed. The planning system of this invention inherently accommodates movement of the anatomical portion being treated, in that the real time output of the scanner is continuously captured and displayed. The movement is typically caused by the implantation process itself and can be taken into account by subsequent needle placement during the process of FIG. 3. It is therefore seen that the planning system of this invention inherently assures improved maintenance of proper registration of the implant with respect to the treated anatomical portion. When a sufficient number of needles or guide tubes have been implanted and an acceptable plan generated for all of the needles, the dosage level is checked by the medical personnel at step 329, and if found unacceptable, the normalization of the dwell times is changed at step 331 until the dose is found to be satisfactory.

Next, at step 333, the position of the anatomical portion such as the prostate is rechecked via ultrasound scanner 201 of FIG. 2, and if it has been found to have been moved by the implantation of the guide tubes or needles, then the needles are advanced at step 337 into their proper relative positions with respect to the anatomical portion to be treated. If the position of the anatomical portion is acceptable, then the final dosage treatment plan is printed and/or downloaded directly to delivery element 113 of FIG. 1, and actual radiation treatment of the anatomical portion can begin.

Figure 4:
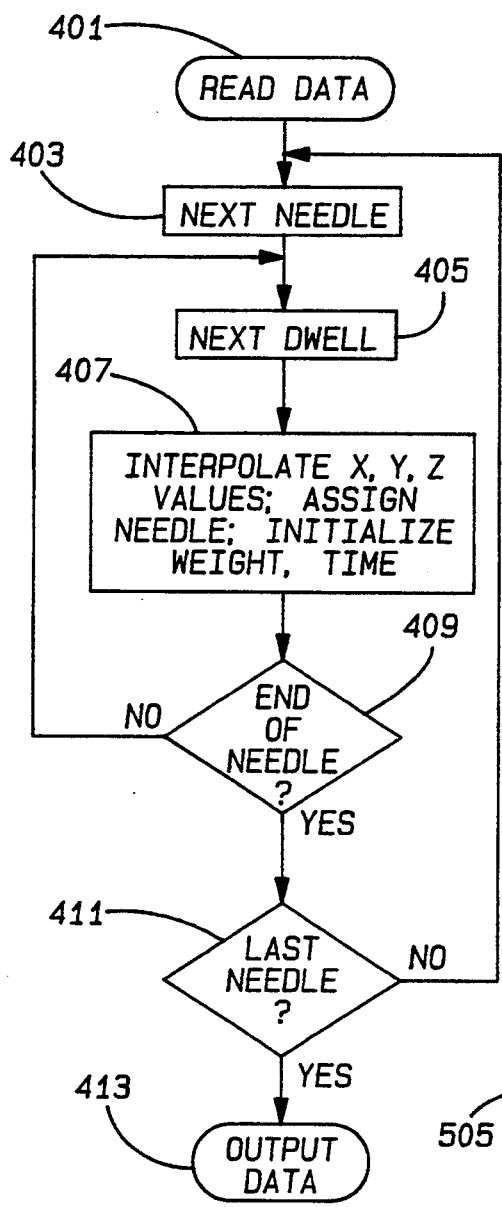
FIG. 4 is a flow chart setting forth further details of the video data based reconstruction of radiation source coordinate data step of FIG. 3.

The video based reconstruction step 319 of FIG. 3 is set forth in further detail of the flow chart of FIG. 4. Basically, this routine generates a model of the three dimensional structure of the dwell positions in the plurality of guide tubes or needles that have been implanted. Input data to the routine of FIG. 4 includes the number of guide tubes or needles, the active length of each, the depth or location along the y axis of a reference scanning plane, the length of each indexable step of a radiation source in each guide tube and, for each needle, an identification or ordinal number, its coordinate in the x,z plane at a positioning template and, the x,z coordinates of the needle at the reference scan plane.

Video reconstruction or modeling from a transverse ultrasound scan is illustrated. A series of guide tubes or needles are placed using the template with known spacing between guide holes (e.g. a rectangular array 5 millimeters on center). An ultrasound scanner using an intracavitary probe is used to image the needles transverse to their length. By moving the probe in or out using a carriage, the depth of the ends of the guide tubes or needles may be determined. This is used to establish an origin of the y axis. The length of a tumor volume is likewise determined, thus determining the range of y values (i.e. the "active length") to be treated along each needle. The transverse plane or x,z positions of the needles are known at the level of the template, due to its known geometry. Another set of x and z coordinates are measured from a transverse scan at a known depth (y). From the two points x,y,z (template) and x,y,z (reference scan), a vector is constructed for each needle which allows the x and z components to be interpolated from the template and reference values for any value along the y axis. The radiation source dwell positions can then be determined by stepping off the proper distance along each guide tube or needle and recording the resulting x,y,z coordinate and current needle number at each step. The final output of the routine is a count of the dwell positions and a data structure which lists, for each dwell position, its identification or ordinal number (i.e. a number within the implant as a whole), the identification of the needle that the dwell position resides in and the spatial cartesian coordinates of the dwell position.

With reference to FIG. 4, the reconstruction basic steps comprise reading the input data at step 401, selecting a next needle at step 403 and a next dwell position within that needle at step 405. Then at step 407, utilizing the template and reference positional data, the x,y,z cartesian coordinate values for the dwell position of interest are interpolated at step 407, and an initial weight and dwell time in relative unitless values are assigned. This interpolation process is repeated for every dwell position in the implant using the tests at steps 409 and 411, and when all dwell positions have been modeled, the data is output at step 413.

Figure 5:
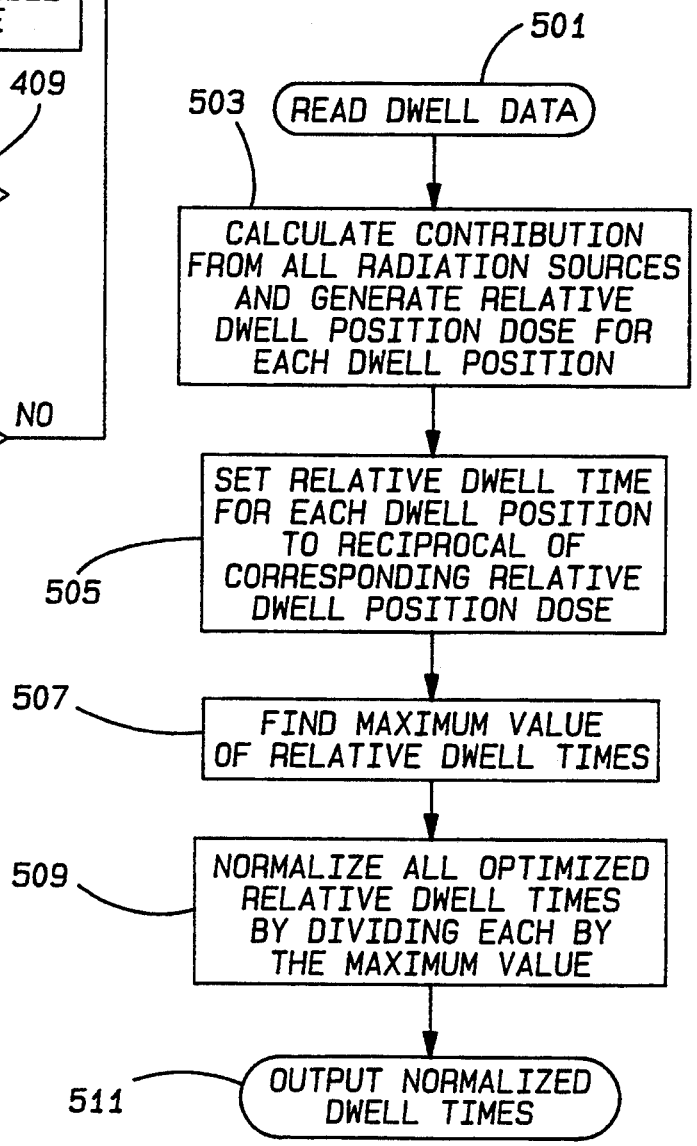
FIG. 5 is a flow chart setting forth further details of the radiation source dwell time optimization step of FIG. 3.

The geometric optimization of relative radiation source dwell times at each dwell position in the implant is performed at step 321 of FIG. 3, and the details of the optimization method are set forth in the flow chart of FIG. 5. Geometric optimization is method for providing either a uniform or other distributed radiation dose throughout the anatomical portion implanted with the guide tubes.

With reference to FIG. 5, the dwell data generated in the previous reconstruction step 319 of FIG. 3 is read and, for each dwell position, a relative dwell position radiation dose is generated by calculating the contribution to the radiation dose level at the dwell position of interest from all other radiation source locations in other guide tubes in the implant. This calculation is performed at step 503 and is based upon the known principle that a relative dose level is proportional to the inverse square of the distance between the dwell position of interest and other dwell positions in the implant.

At step 505 of FIG. 5 a relative dwell time for each dwell position is set equal to the reciprocal of the corresponding relative dwell position dose calculated at step 503. Next, at step 507, a maximum value of the relative dwell time generated at step 505 is determined, and at step 509 all the relative dwell times are then normalized by dividing each by the determined maximum value. The output dwell times are then passed on to the further normalization step of FIG. 3 at step 511 of FIG. 5.

Figure 6:
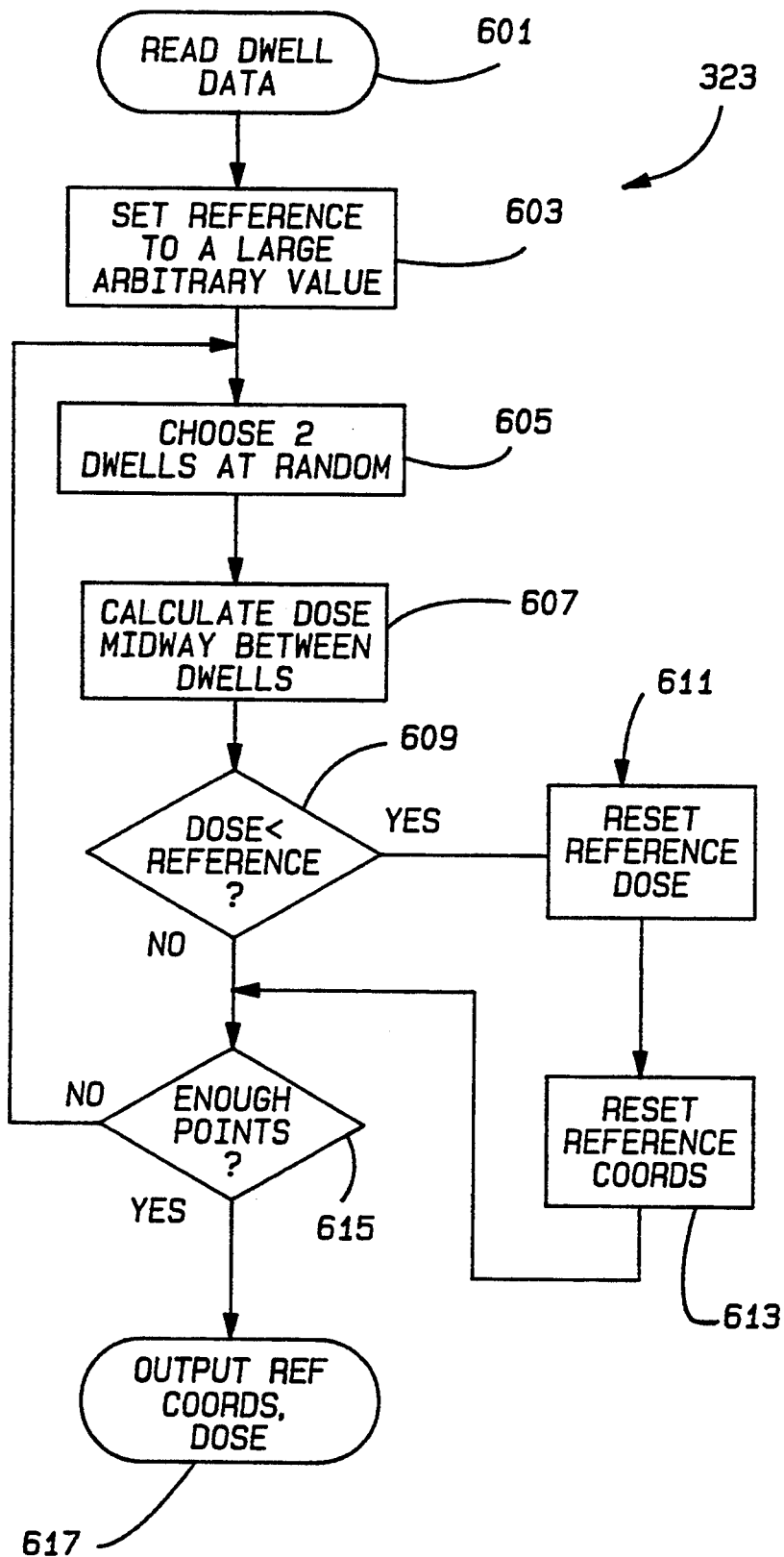
FIG. 6 is a flow chart setting forth further details of the normalization step of FIG. 3.

Further details of the normalization step 323 of FIG. 3 are set forth in the flow chart of FIG. 6. Normalization is a method for determining a normalization factor for a tissue volume treated with radiation sources positioned in accordance with the geometric optimization step 321 of FIG. 3. Such a normalization factor is necessary, because the optimization step only determines relative dwell times, not actual times to be used for treatment. The normalization factor is arbitrary. However, the factor may be adjusted later by the medical personnel in order to "fine tune" the delivered dosage. (E.g.—see steps 329 and 331 of FIG. 3).

Normalization to the minimum dose in the treated anatomical volume provides a highly automated method of dose prescription, consistent with a goal of producing a complete treatment plan immediately after the placement of each individual implant guide tube or needle. This allows the medical personnel to base needle placement decisions on the actual dose distributions presented at a display in real time (and overlaying an image of the anatomy to be treated) rather than relying solely upon arbitrary placement rules, which may not produce ideal dosage distributions or accurate registration with the intended anatomical volume.

The normalization routine generates dose calculation points midway between pairs of randomly selected dwell positions. This is an efficient search mechanism for finding local dose minima in volume implants for anatomical portions having external surfaces with no concave cavities—i.e. having a convex configuration. The normalization method assumes that the number of dwell positions, a prescribed dose level, current source strength and dwell times are available as input. Each dwell position is known by its identification number and coordinate data generated in the reconstruction step 319 of FIG. 3.

With reference to FIG. 6, the dwell data is read at step 601 and a reference dose is set to a large arbitrary value that is selected in accordance with empirically determined guide lines. At step 605 two dwell positions within the implant model are chosen at random and a dose is calculated at a point midway between the selected dwell positions at step 607. Again, this conventional calculation is generally based on the principle that the dose level at a given point is proportional to the inverse of the square of the distance from the source. Next, the method determines the minimum of the calculated doses at steps 609 and 615 wherein, if a calculated dose is less the reference dose value, then the reference dose value becomes that calculated dose and the reference point is then selected to have the coordinates of the present dose calculation point under consideration. The adjustments of the reference dose and reference coordinates are effected at steps 611 and 613. When the minimum dose has been determined, then its corresponding reference coordinates and the minimum dosage are output at step 617. The normalization factor is then calculated as the prescribed dose divided by the minimum dose determined by the routine.

The position of the reference point is displayed to the user, as it is possible for the reference point to lie outside the volume of the anatomical portion, if such volume has concave surface portions. In such a case the normalization will require a relatively large adjustment. If the normalization point is within the volume of the anatomical portion to be treated, an adjustment larger than plus or minus 10 percent constitutes a quality assurance "caution" flag. Actual dwell times for the radiation source are then derived from the relative dwell times by multiplying each relative dwell time determined in step 321 of FIG. 3 by the normalization factor generated by the routine of FIG. 6.

After medical personnel verify, from observing an overlaid dosage profile superimposed on an image of the pertinent anatomy, that the implant geometry is acceptable, a typical plan output in hard copy form may be generated and typically comprises specification of a prescribed dose, a reference point within the implant which receives the minimum or reference dose and a normalization factor with which the user may determine actual dwell times by multiplying the relative dwell times listed by the normalization factor.

Using the principles of the invention to rapidly generate a dosage treatment plan, a prototype system has been used for prostate gland treatment, and the initiation of the actual radiation treatment has been effected within 10 to 15 minutes of final needle placement. The dosage plan generation time has been reduced from on the order of one hour, using conventional prior art techniques, to approximately 1 second for a typical implant of 15 guide tubes or needles of approximately four centimeters active length.

The invention has been described with reference to a detailed description of a preferred embodiment. These details have been set forth for the sake of example and the scope of the invention is to be determined solely by proper interpretation of the appended claims.

It is to be noted that this invention is additionally contemplated for use as a determinant of implant source positioning with other types of implant therapy, such as temporary continuous brachytherapy (using on the order of days of implantation time) or permanent implant therapy.

I claim:

1. A real time radiation treatment dosage planning system for use in effecting radiation therapy of a preselected anatomical portion of an animal body, the system comprising:

radiation delivery means for defining a plurality of positions having a spatial relationship within a volume of the anatomical portion and for placing a radiation source at said plurality of positions;

imaging means for generating real time visual image data corresponding to the anatomical portion;

means responsive to the real time visual image data for monitoring said plurality of positions to detect a change in the spatial relationship of said positions;

processing means for automatically generating, in response to a detected change in the spatial relationship of said positions, a treatment plan including a generated value of the radiation source and a generated time period the radiation source is to be placed at each position by the radiation delivery means.

2. The system of claim 1, wherein the processing means further comprises means for generating a visual representation of a radiation dosage distribution effected by the radiation source value and time periods and for superimposing the visual representation over an image of the anatomical portion.

3. The system of claim 1, wherein the processing means further comprises means for transmitting the time periods to the radiation delivery means.

4. The system of claim 3, wherein the radiation delivery means includes a plurality of guide tubes arranged for insertion into the anatomical portion, a radiation source adjustably positionable within the tubes and control means for varying a position of the radiation source within the tubes, and wherein the means for automatically generating produces a plurality of indications of positions within the tubes and a dwell time for each position of the radiation source.

5. The system of claim 1, wherein the imaging means comprises an ultrasound scanner.

6. The system of claim 1, wherein the radiation delivery means includes a plurality of guide tubes arranged for insertion into the anatomical portion, a radiation source adjustably positionable within the tubes and control means for varying a position of the radiation source within the tubes, and wherein the means for automatically generating produces a plurality of indications of positions within the tubes and a dwell time for each position of the radiation source.

7. The system of claim 6, wherein the imaging means comprises an ultrasonic scanner.

8. The system of claim 7, wherein the anatomical portion comprises a human prostate gland.

9. In a therapy system for applying radiation to a preselected anatomical portion of an animal body by using means responsive to control data for indexing a position and holding each position for predetermined time periods of a radiation source within a plurality of guide members inserted into the anatomical portion, placement of each guide member with respect to the anatomical portion being monitored by scanning means, the improvement comprising:

processing means including means coupled to the scanning means for capturing real time visual image data generated thereby and using said real time visual image data to monitor said plurality of positions to detect a change in the spatial relationship of said positions, and means for automatically generating, in response to a detected change in the spatial relationship of said positions, revised control data for use by the means for indexing and indicating each indexed position of the radiation source within the plurality of guide members and each dwell time of the source at each indexed position.

10. The improvement of claim 9, wherein the processing means further comprises means for generating a visual representation of a radiation dosage distribution profile effected by use of the control data by the means for indexing and superimposing the visual representation over an image of the anatomical portion.

11. The improvement of claim 10, wherein the processing means further comprises means for transmitting the control data to the means for indexing.

12. The improvement of claim 9, wherein the scanning means comprises an ultrasound scanner.

13. The improvement of claim 12, wherein the anatomical portion comprises a human prostate gland.

14. A method for generating a radiation treatment dosage plan for use in applying radiation to a preselected anatomical portion of an animal body by a radiation delivery system operable to place a radiation source in a plurality of positions within a volume of the anatomical portion, the method comprising:

generating real time visual image data corresponding to the anatomical portion with a scanner;

capturing the real time visual image data at a stored program processor and automatically generating, using the captured real time visual data, a time period during which the radiation source is to be placed at each of the plurality of positions;

monitoring the real time visual image data to detect a change in at least one of said plurality of positions and, in response to a detected change, automatically regenerating said time period during which the radiation source is to be placed at each of the plurality of positions; and transmitting an indication of the value of the time periods to the radiation delivery system.

15. The method of claim 14, further comprising the step of generating a visual representation of a radiation dosage distribution effected by the time periods and radiation source and superimposing the visual representation over a displayed image of the anatomical portion.

16. The method of claim 14, wherein the scanner comprises an ultrasonic scanner.

17. The method of claim 16, wherein the anatomical portion comprises a human prostate gland.

18. A method for generating a radiation treatment dosage plan for use in applying radiation to a preselected anatomical portion of an animal body with a radiation source indexable to a plurality of dwell positions within each of a plurality of guide tubes inserted at a plurality of locations within the anatomical portion, the method comprising:

(a) generating real time visual image data corresponding to the anatomical portion with a scanner;

(b) selecting a location within the anatomical portion for one of the guide tubes and placing the one guide tube at the selected location;

(c) generating, with the scanner, real time visual image data of the location selected in step (b) and combining it with the visual image data corresponding to the anatomical portion and to any previously positioned guide tubes;

(d) capturing the real time visual image data generated by steps (a) and (c) and automatically generating, using the captured image data, a dwell time period for each position of the radiation source within all guide tubes currently in place; and (e) repeating steps (b) through (d) for successive ones of the plurality of guide tubes while automatically revising dwell time periods previously generated, in response to a change in position of any previously positioned guide tubes, until a volume of the anatomical portion is enveloped by a preselected radiation dose profile.

19. The method of claim 18, wherein step (d) further comprises:

(i) reconstructing dimensional coordinates of all dwell positions for all previously considered locations of guide tubes and a currently selected guide tube;

(ii) optimizing and normalizing relative dwell times of the radiation source at each dwell position of all guide tubes currently in place; and (iii) generating a normalization factor for converting relative dwell times to actual dwell times for maintaining the radiation source at each dwell position of each guide tube currently in place.

20. The method of claim 19, wherein the step of reconstructing further comprises:

using a template of guide holes with known geometry to hold the guide tubes;

using scanner data to determine a depth of each guide tube within the anatomical portion;

using coordinates of each guide tube at the template and at a known reference scanning plane transverse to lengths of the guide tubes to interpolate coordinates for every dwell position in each guide tube; and for each dwell position, saving a dwell number, guide tube number and interpolated three dimensional coordinates.

21. The method of claim 20, wherein the step of optimizing further comprises:

for each dwell position, calculating a dwell time value as a function of contributions of the radiation source positioned at all other dwell positions not within the same guide tube;

determining a maximum value of calculated dwell times; and normalizing each calculated dwell time to the maximum value.

22. The method of claim 21, wherein the step of generating a normalization factor further comprises:

(1) assigning a preselected number as a reference dose at a reference location;

(2) selecting two dwell locations at random from all dwell locations of all guide tubes currently in place;

(3) calculating a dose value at a point midway between the randomly selected dwell locations;

(4) comparing the calculated dose value to the reference dose and whenever the calculated dose value is less than the reference dose, setting the reference dose equal to the calculated dose and the reference location equal to the point midway between the randomly selected dwell locations;

(5) repeating steps (1) through (4) for a preselected number of times; and (6) setting a normalization factor equal to a prescribed dose divided by the reference dose.

* * * * *